United States Patent [19]

Ranken et al.

[11] Patent Number: 4,552,966

[45] Date of Patent: Nov. 12, 1985

[54] 2-NITRO-4-(4-PYRIDINYL) BENZOIC ACIDS AND DERIVATIVES

[75] Inventors: Paul F. Ranken; Thomas J. Walter, both of Baton Rouge, La.

[73] Assignee: Ethyl Corporation, Richmond, Va.

[21] Appl. No.: 511,844

[22] Filed: Jul. 8, 1983

[51] Int. Cl.[4] .................. C07D 211/72; C07D 215/16; C07D 265/26

[52] U.S. Cl. ..................................... 546/290; 546/156; 546/157; 546/161; 546/296; 546/335; 546/345; 544/94

[58] Field of Search .................. 544/94; 546/156, 161, 546/335, 157

[56] References Cited

U.S. PATENT DOCUMENTS 3,753,993  8/1973  Lesher ............................ 260/286 R
3,907,808  9/1975  Lesher ................................ 424/258
4,118,557 10/1978  Lesher ................................ 542/420

OTHER PUBLICATIONS

Mitscher et al., J. Med. Chem. 1978, vol. 21, No. 5, pp. 485–489.

March, Advanced Organic Chem. 2nd edition, pp. 1096–1097.

Morrison, Organic Chem. p. 441.

*Primary Examiner*—Donald G. Daus
*Assistant Examiner*—Cecilia Shen
*Attorney, Agent, or Firm*—Donald L. Johnson; John F. Sieberth; Patricia J. Hogan

[57] ABSTRACT

2-Nitro-4-(4-pyridinyl)benzoic acids, such as 2-nitro-4-(4-pyridinyl)benzoic acid, are prepared by oxidizing the appropriate 4-(4-alkyl-3-nitrophenyl)pyridine with, e.g., potassium permanganate or nitric acid. The products are particularly useful in the preparation of antibacterial 1-alkyl-1,4-dihydro-4-oxo-7-pyridinyl-3-quinolinecarboxylic acids.

4 Claims, No Drawings

2-NITRO-4-(4-PYRIDINYL) BENZOIC ACIDS AND DERIVATIVES

FIELD OF THE INVENTION

This invention relates to 2-nitro-4-(4-pyridinyl)benzoic acids, a process for preparing them, and processes for preparing derivatives thereof.

BACKGROUND

As disclosed in Sterling Drug's U.S. Pat. Nos. 3,753,993 (Lesher et al.), 3,907,808 (Lesher and Carabateas), and 4,118,557 (Lesher), it is known that antibacterial 1-alkyl-1,4-dihydro-4-oxo-7-pyridinyl-3-quinolinecarboxylic acids can be prepared from 4-(3-aminophenyl)pyridine. It is also known that this route to the bactericides, as disclosed, is less economical than might be desired.

From Mitscher et al., "Quinoline Antimicrobial Agents. 1. Versatile New Synthesis of 1-Alkyl-1,4-dihydro-4-oxo-3-quinolinecarboxylic Acids," *Journal of Medicinal Chemistry*, 1978, Vol. 21, No. 5, pp. 485–489, it is also known that antimicrobial agents related to the aforementioned bactericides can be prepared from the appropriate isatoic anhydrides.

It would be desirable to be able to prepare the antibacterial agents of Lesher, Lesher et al, and Lesher and Carabateas by a route similar to that employed by Mitscher et al. However, although, as indicated in copending application Ser. No. 511,887, filed July 8, 1983, in the name of Thomas J. Walter (Walter), this route to the antibacterial agents can be employed when 4-(4-alkyl-3-nitrophenyl)pyridines are utilized, it has previously been found difficult to convert the 4-(4-alkyl-3-nitrophenyl)pyridines to the acids, salts, or esters required for conversion to suitable isatoic anhydrides. Heretofore, the only technique that has been successfully employed in converting the 4-(4-alkyl-3-nitrophenyl)pyridines to suitable acids, salts, or esters has been the process taught in copending application Ser. No. 511,854, filed July 8, 1983, in the name of V. Ramachandran—a process in which the 4-(4-alkyl-3-nitrophenyl)pyridine is treated with an alcoholic base to produce a 2-amino-4-(4-pyridinyl)benzoic acid.

SUMMARY OF INVENTION

An object of this invention is to provide 2-nitro-4-(4-pyridinyl)benzoic acids which are convertible to 1-alkyl-1,4-dihydro-4-oxo-7-pyridinyl-3-quinolinecarboxylic acids via isatoic anhydrides.

Another object is to provide a process for preparing the 2-nitro-4-(4-pyridinyl)benzoic acids.

A further object is to provide a process for preparing derivatives of the 2-nitro-4-(4-pyridinyl)benzoic acids.

These and other objects are attained by oxidizing a 4-(4-alkyl-3-nitrophenyl)pyridine to a 2-nitro-4-(4-pyridinyl)benzoic acid and, when appropriate, converting the acid to a desired derivative thereof.

DETAILED DESCRIPTION 4-(4-Alkyl-3-nitrophenyl)pyridines utilizable in the practice of the invention are compounds corresponding to the formula:

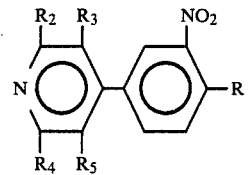

wherein R is alkyl, e.g., a methyl or other alkyl group containing 1–6 carbon atoms, and $R_2$, $R_3$, $R_4$, and $R_5$ are independently selected from hydrogen and innocuous substituents, such as substituted (e.g., halogenated) and unsubstituted aryl or aryloxyaryl groups, halo, etc. These compounds are preferably prepared by the process taught in Walter, the teachings of which are incorporated herein by reference. As indicated in Walter, the preferred 4-(4-alkyl-3-nitrophenyl)pyridine, when the aforementioned bactericides are to be prepared, is 4-(4-methyl-3-nitrophenyl)pyridine.

The 4-(4-alkyl-3-nitrophenyl)pyridine, although not oxidizable by many known techniques, may be oxidized by certain conventional techniques, i.e., the use of potassium permanganate or concentrated nitric acid, as taught in March, *Advanced Organic Chemistry*, McGraw-Hill (New York), 1977, pp. 1096–1097. In a preferred embodiment of the invention, the oxidation is accomplished by treating the 4-(4-alkyl-3-nitrophenyl)pyridine with at least two molar proportions of aqueous potassium permanganate per molar proportion of the starting material under reflux conditions in the presence of t-butanol to form a potassium salt of a 2-nitro-4-(4-pyridinyl)benzoic acid. This salt may be used per se in the production of the aforementioned bactericides, or it may be first converted to the corresponding acid (e.g., by HCl acidification) or to a corresponding ester (e.g., by dissolving it in the appropriate alkanol, treating it with anhydrous HCl, and refluxing the resultant solution).

The 2-nitro-4-(4-pyridinyl)benzoic acids formed in the process of the invention are compounds corresponding to the formula:

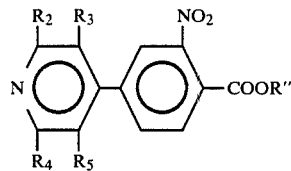

wherein R" is hydrogen, an alkali metal, or an alkyl group containing 1–6 carbon atoms, and $R_2$, $R_3$, $R_4$, and $R_5$ have the same definitions as given above. When the aforementioned bactericides are to be prepared, the preferred product is 2-nitro-4-(4-pyridinyl)benzoic acid or an alkali metal salt or alkyl ester thereof. These compounds are useful in the synthesis of a variety of materials but are particularly useful as intermediates in the production of the antibacterial 1-alkyl-1,4-dihydro-4-oxo-7-pyridinyl-3-quinolinecarboxylic acids of Lesher, Lester et al., and Lesher and Carabateas, i.e., compounds corresponding to the formula:

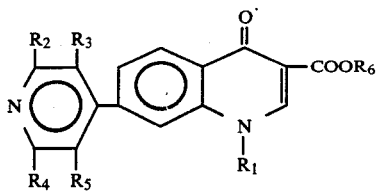

wherein $R_6$ is hydrogen or alkyl, $R_1$ is alkyl, haloalkyl, or hydroxyalkyl, and $R_2$, $R_3$, $R_4$, and $R_5$ have the same definitions as given above—any aliphatic groups generally containing 1-6 carbons.

The synthesis of these bactericides from the 2-nitro-4-(4-pyridinyl)benzoic acids may be accomplished by conventional techniques, e.g.:

(1) 2-nitro-4-(4-pyridinyl)benzoic acid or a salt or ester thereof can be reduced to the corresponding amino compound,
(2) the 2-amino-4-(4-pyridinyl)benzoic acid, salt, or ester can be converted to 4-(4-pyridinyl)isatoic anhydride, e.g., by reaction with phosgene,
(3) the 4-(4-pyridinyl)isatoic anhydride can be N-alkylated, generally N-ethylated, by reaction with a suitable alkylating agent, e.g., the appropriate organic halide,
(4) the resultant N-alkyl-4-(4-pyridinyl)isatoic anhydride may be reacted with an alkali metal salt of an alkyl (e.g., ethyl) formyl acetate to form an alkyl 1-alkyl-1,4-dihydro-4-oxo-7-pyridinyl-3-quinolinecarboxylate, e.g., ethyl 1-ethyl-1,4-dihydro-4-oxo-7-pyridinyl-3-quinolinecarboxylate, and
(5) the alkyl 1-alkyl-1,4-dihydro-4-oxo-7-pyridinyl-3-quinolinecarboxylate may then be hydrolyzed to the corresponding 1-alkyl-1,4-dihydro-4-oxo-7-pyridinyl-3-quinolinecarboxylic acid.

The following examples are given to illustrate the invention and are not intended as a limitation thereof.

EXAMPLE I

A hot (60°–70° C.) solution of 2.5 molar proportions of potassium permanganate in 135.3 molar proportions of water was added over a period of six hours to a stirred, refluxing solution of one molar proportion of 4-(4-methyl-3-nitrophenyl)pyridine in 32.5 molar proportions of water and 13.1 molar proportions of t-butanol. The reaction mixture was stirred and refluxed until the permanganate color discharged and was then stirred at room temperature overnight.

The t-butanol was removed by distillation, and manganese dioxide was removed by suction filtration of the hot reaction mixture. The filter cake was slurried twice with 20.9 molar proportions of water and then twice with 6.1 molar proportions of methylene chloride. The filtrate and the aqueous wash were combined and extracted three times with 6.1 molar proportion aliquots of methylene chloride. The extracts were combined with the organic wash of the filter cake and the solvent removed to recover 29% of the starting material, indicating a conversion of 71%.

The pH of the aqueous phase was adjusted to 5.0 with HCl, and the white precipitate was collected by suction filtration. The solid was washed successively with water and acetone and then dried to provide a 70% yield of 2-nitro-4-(4-pyridinyl)benzoic acid as a white solid. After recrystallization from N,N-dimethylformamide, the white crystals were determined to have a melting point of 314°–316° C.

EXAMPLE II

A mixture of 10 mmols of 4-(4-methyl-3-nitrophenyl)pyridine and 30 ml of 70% nitric acid was refluxed overnight, after which the reaction vessel was placed on a steam bath, and the nitric acid was removed under a flow of nitrogen. The residue was neutralized to a pH of about 10 with sodium carbonate, extracted with methylene chloride, and dried over sodium sulfate. After removal of the solvent, the aqueous pH was adjusted to 4, and the product was isolated by filtration. The reaction resulted in a 44% conversion of starting material and a 48% yield of 2-nitro-4-(4-pyridinyl)benzoic acid.

EXAMPLE III

A mixture of 47 mmols of 4-(4-methyl-3-nitrophenyl)pyridine and 100 ml of 70% nitric acid was refluxed for three days and worked up, essentially as in Example II, to result in a 68% conversion of starting material and the isolation of 2-nitro-4-(4-pyridinyl)benzoic acid in 61% yield.

It was found that the 2-nitro-4-(4-pyridinyl)benzoic acid prepared in the preceding examples could be converted to 1-ethyl-1,4-dihydro-4-oxo-7-pyridinyl-3-quinolinecarboxylic acid by (a) reducing it to 2-amino-4-(4-pyridinyl)benzoic acid, (b) reacting the 2-amino-4-(4-pyridinyl)benzoic acid with phosgene to form 4-(4-pyridinyl)isatoic anhydride, (c) alkylating the 4-(4-pyridinyl)isatoic anhydride with ethyl bromide to produce N-ethyl-4-(4-pyridinyl)isatoic anhydride, (d) reacting the N-ethyl-4-(4-pyridinyl)isatoic anhydride with the potassium salt of ethyl formyl acetate to form ethyl 1-ethyl-1,4-dihydro-4-oxo-7-pyridinyl-3-quinolinecarboxylate, and (e) hydrolyzing that ester.

It is obvious that many variations may be made in the products and processes set forth above without departing from the spirit and scope of this invention.

We claim:

1. A compound corresponding to the formula:

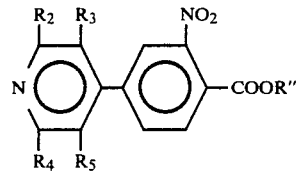

wherein R″ is hydrogen, an alkali metal, or an alkyl group containing 1–6 carbons, and $R_2$, $R_3$, $R_4$, and $R_5$ are independently selected from hydrogen and aryl, aryloxyaryl, and halo substituents.

2. 2-Nitro-4-(4-pyridinyl)benzoic acid.
3. Ethyl 2-nitro-4-(4-pyridinyl)benzoate.
4. Potassium 2-nitro-4-(4-pyridinyl)benzoate.

* * * * *